United States Patent [19]

Flentge

[11] Patent Number: 4,559,173

[45] Date of Patent: Dec. 17, 1985

[54] N-SUBSTITUTED DIBENZ[B,F]AZEPINE SALTS

[75] Inventor: Charles A. Flentge, Lake Villa, Ill.

[73] Assignee: Abbott Laboratories, North Chicago, Ill.

[21] Appl. No.: 548,742

[22] Filed: Nov. 4, 1983

[51] Int. Cl.$^4$ .......................................... C07D 223/22
[52] U.S. Cl. .............................................. 260/239 D
[58] Field of Search ...................... 260/239 D, 239 BE

[56] References Cited

U.S. PATENT DOCUMENTS 3,510,476  5/1970  Davis .............................. 260/239 D
4,273,866  6/1981  Voss et al. ......................... 435/810

Primary Examiner—Glennon H. Hollrah
Assistant Examiner—D. B. Springer
Attorney, Agent, or Firm—Martin L. Katz; Margaret M. O'Brien; James L. Wilcox

[57] ABSTRACT

Carbamazepine-thiophosphonate conjugates for use as enzyme inhibitors having the formula:

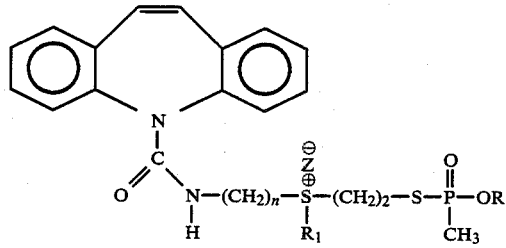

wherein Z is a biologically compatible counter ion, n is an integer from 2 to 6 and R and $R_1$ are each lower alkyl.

7 Claims, No Drawings

N-SUBSTITUTED DIBENZ[B,F]AZEPINE SALTS

This invention relates to carbamazepine conjugates, and more particularly to carbamazepine-thiophosphonate conjugates for use as enzyme tracers.

There is described in U.S. Pat. No. 4,273,866 a technique for determining the presence of ligands in test samples in which a test sample is mixed with a ligand analog-irreversible enzyme inhibitor conjugate as well as a binding protein bindable to the ligand and the ligand analog-irreversible inhibitor conjugate. As described in that patent, the amount of ligand analog-irreversible enzyme inhibitor conjugate bound by the binding protein is related to the amount of ligand test sample. Thus, the techniques as described in that patent provide a convenient immunoassay technique for measuring the amount of a variety of drugs, hormones and the like biological fluids.

The present invention relates to novel conjugates of carbamazepine which can be used in the immunoassay technique described in the foregoing patent.

The concepts of the present invention reside in compounds having the formula:

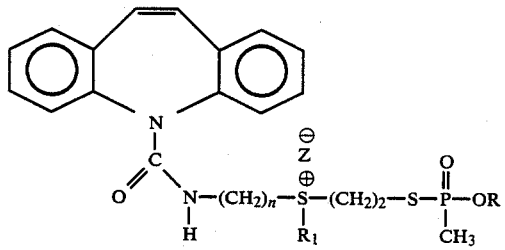
(I)

wherein Z is a biologically compatible counter ion, n is an integer from 2 to 6 and R and $R_1$ are each independently a lower alkyl group, and preferably one containing 1 to 5 carbon atoms (e.g., methyl, ethyl, propyl, n-butyl, tert-butyl, etc.).

As used herein, the term "biologically compatible counter ion" refers to anions represented by "Z" including, for example, chloro, iodo, methylsulfate, tetrafluoroborate and the like.

The compounds of the present invention are useful as tracers for acetylcholinesterase in immunoassays for the determination of carbamazepine in serum or plasma. Such compounds can be used, for example, in the immunoassay technique described in U.S. Pat. No. 4,273,866, the disclosure of which is incorporated herein by reference.

The compounds of the present invention are prepared using standard synthetic techniques. Iminostilbene is first reacted with phosgene to form the corresponding acetyl chloride derivative as illustrated by the following:

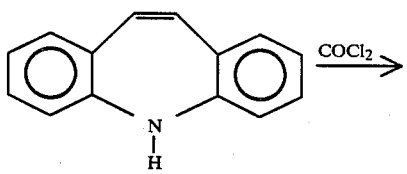
(II)

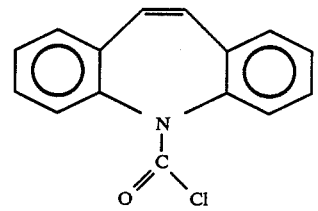

In a separate step, an n-butoxycarbonyl protected phosphonate is, in accordance with the teachings of U.S. Pat. No. 4,273,866, converted to the corresponding trifluoroacetic salt as illustrated below:

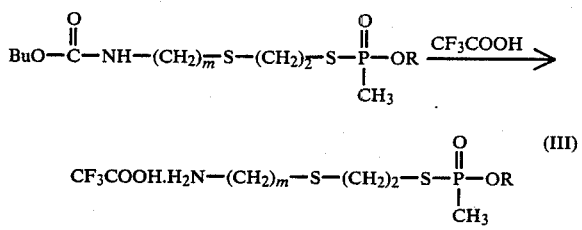

The products (II) and (III) are then reacted in the presence of an amine base:

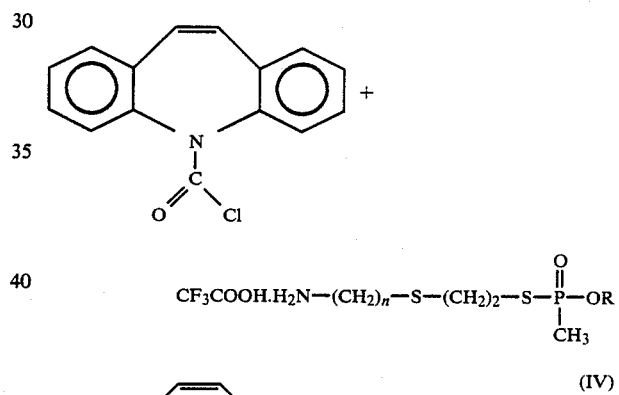

Finally, in the last step, compound IV is reacted with an alkyl iodide and preferably methyl iodide in the presence of a Lewis acid catalyst such as silver tetrafluoroborate to produce the compounds of the invention.

As indicated above, the compounds of the present invention can be used in the immunoassay for carbamazepine in accordance with the techniques described in U.S. Pat. No. 4,273,866. Generally, in the use of the compounds of the invention, the carbamazepine in a serum specimen is mixed with a specific antibody against carbamazepine, the enzyme acetylcholinesterase, the carbamazepine analogs of the present invention, the enzyme substrate which is typically acetyl-beta-(methylthio)choline iodide and a reagent to produce the chromogenic product, usually 5,5'-dithiobis-(2-nitrobenzoic) acid. As those skilled in the art appreciate, the carbamazepine present in the specimen and the carbamazepine analog compete for a limited number of binder sites on the antibody, the degree of binding of each being proportional to their respective concentrations. The carbamazepine analogs of the present invention, which are unbound rapidly and irreversibly, inhibit the enzyme while the analog bound by the antibody has no inhibitory effect on the enzyme. Thus, the amount of enzyme activity which is inhibited is related to the concentration of the carbamazepine in the specimen.

As is described in the foregoing patent, such enzyme activity can be measured colorimetrically. The active enzyme activates the substrate which further reacts to produce a chromogenic product. Spectrophotometric absorbence readings can thus be made, the intensity of the carbamazepine being present in the specimen.

The immunoassay can be performed at ambient temperatures although, as will be appreciated by those skilled in the art, temperatures ranging from ambient to physiological temperatures can be used with facility. Reaction times are dependent on temperature and reagent dilution.

Having described the basic concepts of the present invention, reference is now made to the following example which is provided by way of illustration of the practice of the invention of the preparation of the carbamazepine conjugates.

EXAMPLE

Iminostilbene (10 g) is added to toluene and stirred in suspension. Phosgene gas is passed through the solution until all the iminostilbene is dissolved. The solution is refluxed while phosgene is continued for 15 minutes. Phosgene is discontinued and nitrogen is passed through the solution for one hour during cooling. The solid which forms is collected on a filter and dried to yield 5.7 g of the corresponding N-chloroacetyl derivative (II).

The butoxycarbonyl thiophosphonate (V, 4.0 g)

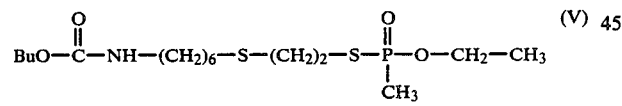

is taken up in methylene chloride (10 ml) and cooled to 0° C. Trifluoroacetic acid (10 ml) is added and the solution is stirred for 30 minutes at 0° C. Solvent is removed to give a quantitative yield of (VI) as an oil

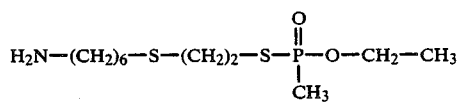

in the form of its trifluoroacetic salt.

The chloroformamide (II, 2.55 g) is dissolved in methylene chloride and added to the thiophosphonate (VI, 2.02 g) in methylene chloride. The reaction is stirred at room temperature for six hours while keeping the pH at 9 using triethylamine. The solution is washed with water, dried with magnesium sulfate and solvent removed. The residue is chromatographed on silica gel eluting with ethyl acetate to give 2.7 g of (VII).

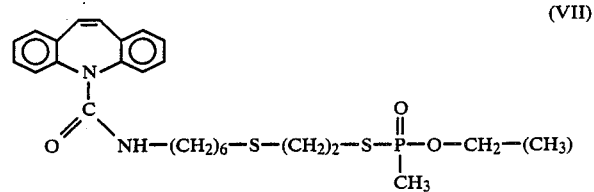

Compound (VII, 2.5 g) is taken up in methylene chloride (5 ml) and cooled to 0° C. Methyl iodide (5 ml) is added followed by silver tetrafluoroborate (1.22 g). The solution is warmed to room temperature, while stirring, for 30 minutes. Silver iodide is filtered off and solvent is removed. The residue is purified on a Waters Prep 500A unit eluting with 80/20/0.01M methanol-water-trifluoroacetic acid on two reversed phase columns to yield 1.56 g of (VIII).

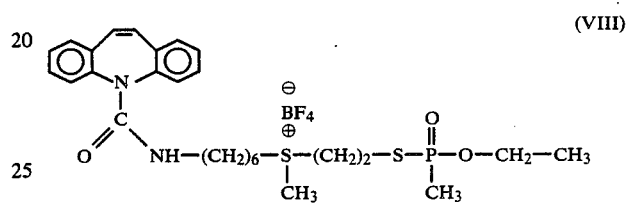

The compound was determined to have a second order rate constant for the inhibition of acetylcholinesterase of $1.8 \times 10^8$ liter mole$^{-1}$ min$^{-1}$.

As will be understood by those skilled in the art, the biologically compatible counter ion is derived from the Lewis acid employed in the last step of the reaction. Other Lewis acids well known to those skilled in the art may be used in lieu of silver tetrafluoroborate, including metal salts containing, as the anion, chloro, iodo and methyl sulfate groups to produce compounds having the corresponding biologically compatible counter ion.

It will be understood that various changes and modifications can be made in the details of procedure, formulation and use without departing from the spirit of the invention, especially as defined in the following claims.

What is claimed is:

1. A compound having the formula:

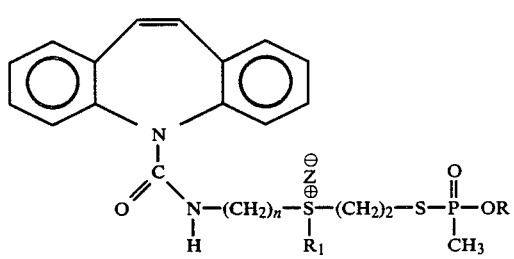

wherein Z is a biologically compatible counter ion, n is an integer from 2 to 6 and R and $R_1$ are each independently lower alkyl.

2. A compound as defined in claim 1 wherein n is 6.
3. A compound as defined in claim 1 wherein R is ethyl.
4. A compound as defined in claim 1 wherein $R_1$ is methyl.
5. A compound as defined in claim 1 wherein n is 6, R is ethyl and $R_1$ is methyl.
6. A compound as defined in claim 1 wherein Z is selected from the group consisting of chloro, iodo, methyl sulfate and tetrafluoroborate ions.
7. A compound as defined in claim 5 wherein Z is the tetrafluoroborate ion.

* * * * *